US009308323B2

(12) United States Patent
Adams

(10) Patent No.: US 9,308,323 B2
(45) Date of Patent: Apr. 12, 2016

(54) SYSTEMS AND METHODS FOR ILLUMINATED MEDICAL TUBING DETECTION AND MANAGEMENT INDICATING A CHARACTERISTIC OF AT LEAST ONE INFUSION PUMP

(75) Inventor: Grant Adams, Coon Rapids, MN (US)

(73) Assignee: SMITHS MEDICAL ASD, INC., Rockland, MA (US)

(*) Notice: Subject to any disclaimer, the term of this patent is extended or adjusted under 35 U.S.C. 154(b) by 599 days.

(21) Appl. No.: 13/495,780

(22) Filed: Jun. 13, 2012

(65) Prior Publication Data

US 2013/0123743 A1   May 16, 2013

Related U.S. Application Data

(63) Continuation-in-part of application No. 13/296,883, filed on Nov. 15, 2011.

(51) Int. Cl.
*G01N 21/85* (2006.01)
*G01N 21/86* (2006.01)
(Continued)

(52) U.S. Cl.
CPC ..... *A61M 5/16831* (2013.01); *A61M 2039/087* (2013.01); *A61M 2205/14* (2013.01);
(Continued)

(58) Field of Classification Search
CPC ............... A61M 5/16831; A61M 2205/14; A61M 2205/18; A61M 2205/6009; A61M 2039/087; A61M 2205/6081; A61M 2205/276; G01N 21/53; G01N 21/532; G01N 21/534; G01N 21/85; G01N 2021/8557; G01N 21/255; G01N 21/05; G01N 2021/052
USPC .............. 250/573, 559.4, 574, 575, 576, 577, 250/221, 222.1, 239; 356/343, 436, 432, 356/440, 441, 442, 218, 222, 239.6; 604/151, 246; 600/139, 152, 156, 158, 600/159, 160
See application file for complete search history.

(56) References Cited

U.S. PATENT DOCUMENTS 2,835,252 A * 5/1958 Mauchel ............. A61M 5/1689
128/DIG. 13
2,954,028 A   9/1960 Smith
(Continued)

FOREIGN PATENT DOCUMENTS

CN     2427205 Y    4/2001
EP     2371411 AI   10/2011
(Continued)

OTHER PUBLICATIONS

Cassano-Piché, Andrea, *Multiple Line Management*, Health Technology Safety Research Team: University Health Network, Jan. 26, 2012, 31 pages.
(Continued)

*Primary Examiner* — Que T Le
*Assistant Examiner* — Jennifer Bennett
(74) *Attorney, Agent, or Firm* — Patterson Thuente Pedersen, P.A.

(57) ABSTRACT

A system for medical tubing detection and management could include an infusion manifold housing having at least one fluid channel therethrough. At least one fluid input port could be provided in the infusion manifold housing and could be configured to connect fluidically to illuminated medical tubing and communicate with the at least one fluid channel through the infusion manifold housing. A fluid output port could be provided in the infusion manifold housing and be configured to be in fluidic communication with the at least one fluid channel through the infusion manifold housing. At least one photosensor could be provided in the infusion manifold housing and be configured to receive light from the illuminated medical tubing; and the fluid output port could be configured to connect fluidically to fluid output tubing.

8 Claims, 7 Drawing Sheets

(51) Int. Cl.
*A61M 5/00* (2006.01)
*A61M 5/168* (2006.01)
*A61M 39/08* (2006.01)

(52) U.S. Cl.
CPC ...... *A61M2205/18* (2013.01); *A61M 2205/276* (2013.01); *A61M 2205/6009* (2013.01); *A61M 2205/6081* (2013.01)

(56) References Cited

U.S. PATENT DOCUMENTS

| | | | |
|---|---|---|---|
| 3,935,876 A | 2/1976 | Massie | |
| 4,009,382 A | 2/1977 | Nath | |
| 4,056,724 A * | 11/1977 | Harte | 250/328 |
| 4,074,187 A | 2/1978 | Miller | |
| 4,447,230 A | 5/1984 | Gula | |
| 4,512,764 A | 4/1985 | Wunsch | |
| 4,524,320 A | 6/1985 | Brooks | |
| 4,559,036 A | 12/1985 | Wunsch | |
| 4,654,026 A | 3/1987 | Underwood | |
| 4,704,660 A | 11/1987 | Robbins | |
| 4,782,430 A | 11/1988 | Robbins | |
| 4,795,429 A | 1/1989 | Feldstein | |
| 4,806,289 A | 2/1989 | Laursen | |
| 4,825,341 A | 4/1989 | Awai | |
| 4,830,461 A | 5/1989 | Ishiharada | |
| 4,900,314 A | 2/1990 | Quackenbush | |
| 4,901,922 A | 2/1990 | Kessenerg | |
| 4,922,385 A | 5/1990 | Awai | |
| 4,957,347 A | 9/1990 | Zarian | |
| 5,016,152 A | 5/1991 | Awai | |
| 5,046,456 A | 9/1991 | Heyman | |
| 5,052,778 A | 10/1991 | Jamshid | |
| 5,067,831 A | 11/1991 | Robbins | |
| 5,118,907 A | 6/1992 | Stout | |
| 5,122,580 A | 6/1992 | Zarian | |
| 5,149,467 A | 9/1992 | Zarian | |
| 5,190,525 A | 3/1993 | Oswald | |
| 5,221,387 A | 6/1993 | Robbins | |
| 5,224,932 A | 7/1993 | Lappas | |
| 5,225,166 A | 7/1993 | Zarian | |
| 5,298,327 A | 3/1994 | Zarian | |
| 5,321,587 A | 6/1994 | Fujita | |
| 5,333,227 A | 7/1994 | Ishiharada | |
| 5,345,531 A | 9/1994 | Keplinger | |
| 5,412,750 A | 5/1995 | Nath | |
| 5,416,875 A | 5/1995 | Keplinger | |
| 5,423,750 A | 6/1995 | Spiller | |
| 5,425,730 A | 6/1995 | Luloh | |
| 5,432,876 A | 7/1995 | Appeldorn | |
| 5,463,706 A | 10/1995 | Dumont | |
| 5,464,025 A | 11/1995 | Charles | |
| 5,479,322 A | 12/1995 | Kacheria | |
| 5,539,624 A | 7/1996 | Dougherty | |
| 5,546,493 A | 8/1996 | Noguchi | |
| 5,557,702 A | 9/1996 | Yoshikawa | |
| 5,631,994 A | 5/1997 | Appeldorn | |
| 5,638,480 A | 6/1997 | Ishiharada | |
| 5,659,643 A | 8/1997 | Appeldorn | |
| 5,684,913 A | 11/1997 | Sugiyama | |
| 5,690,612 A | 11/1997 | Lopez | |
| 5,692,088 A | 11/1997 | Ishiharada | |
| 5,708,749 A | 1/1998 | Kacheria | |
| 5,737,471 A | 4/1998 | Sugiyama | |
| 5,779,353 A | 7/1998 | Kacheria | |
| 5,788,215 A | 8/1998 | Ryan | |
| 5,833,213 A | 11/1998 | Ryan | |
| 5,843,045 A | 12/1998 | DuPont | |
| 5,845,038 A | 12/1998 | Lundin | |
| 5,873,731 A | 2/1999 | Prendergast | |
| RE36,157 E | 3/1999 | Robbins | |
| 5,898,810 A | 4/1999 | Devens | |
| 5,903,695 A | 5/1999 | Zarian | |
| 5,905,826 A | 5/1999 | Benson | |
| 5,933,560 A | 8/1999 | Ishiharada | |
| 5,937,127 A | 8/1999 | Zarian | |
| 5,954,313 A | 9/1999 | Ryan | |
| 5,974,708 A | 11/1999 | Webb et al. | |
| 5,987,199 A | 11/1999 | Zarian | |
| 5,995,690 A | 11/1999 | Kotz | |
| 6,016,372 A | 1/2000 | Fein | |
| 6,030,108 A | 2/2000 | Ishiharada | |
| 6,039,553 A | 3/2000 | Lundin | |
| 6,050,713 A | 4/2000 | O'Donnell | |
| 6,050,715 A | 4/2000 | Hunger | |
| 6,059,768 A | 5/2000 | Friedman | |
| 6,123,442 A | 9/2000 | Freier | |
| 6,158,458 A | 12/2000 | Ryan | |
| 6,169,836 B1 | 1/2001 | Sugiyama | |
| 6,198,872 B1 | 3/2001 | Lipson | |
| 6,215,947 B1 | 4/2001 | Abramowicz | |
| 6,219,480 B1 | 4/2001 | Cassarly | |
| 6,236,797 B1 | 5/2001 | Hotta | |
| 6,251,311 B1 | 6/2001 | Zarian | |
| 6,257,750 B1 | 7/2001 | Strasser | |
| 6,267,492 B1 | 7/2001 | Reid | |
| 6,272,267 B1 | 8/2001 | Hansler | |
| 6,282,355 B1 | 8/2001 | Zarian | |
| 6,289,150 B1 | 9/2001 | Zarian | |
| 6,302,571 B1 | 10/2001 | Davenport | |
| 6,304,693 B1 | 10/2001 | Buelow | |
| 6,314,226 B1 | 11/2001 | Nath | |
| 6,314,227 B1 | 11/2001 | Nath | |
| 6,322,230 B1 | 11/2001 | Medici | |
| 6,350,050 B1 | 2/2002 | Buelow | |
| 6,363,197 B1 | 3/2002 | Zarian | |
| 6,364,538 B1 | 4/2002 | Ishiharada | |
| 6,367,941 B2 | 4/2002 | Lea | |
| 6,382,824 B1 | 5/2002 | Prasad | |
| 6,385,380 B1 | 5/2002 | Friedrich | |
| 6,393,192 B1 | 5/2002 | Koren | |
| 6,453,099 B1 | 9/2002 | Davenport | |
| D465,038 S | 10/2002 | Bragg | |
| 6,526,213 B1 | 2/2003 | Ilenda | |
| 6,543,925 B2 | 4/2003 | Kuykendal | |
| 6,545,428 B2 | 4/2003 | Davenport | |
| 6,546,752 B2 | 4/2003 | Sulcs | |
| 6,589,229 B1 | 7/2003 | Connelly | |
| 6,614,972 B1 | 9/2003 | Lundin | |
| 6,618,530 B1 | 9/2003 | Lundin | |
| 6,623,667 B2 | 9/2003 | Lundin | |
| D486,263 S | 2/2004 | Grothe | |
| 6,863,428 B2 | 3/2005 | Lundin | |
| 6,866,427 B2 | 3/2005 | Robbins | |
| 6,877,877 B2 | 4/2005 | Rodriguez | |
| 6,942,373 B2 | 9/2005 | Buelow | |
| D513,184 S | 12/2005 | Parker | |
| 7,008,071 B2 | 3/2006 | Buelow | |
| 7,029,137 B2 | 4/2006 | Lionetti | |
| 7,049,937 B1 | 5/2006 | Zweig | |
| 7,052,158 B2 | 5/2006 | Rodriquez | |
| 7,163,326 B2 | 1/2007 | Cassarly | |
| 7,163,329 B2 | 1/2007 | Bina | |
| 7,164,819 B2 | 1/2007 | Jenson | |
| 7,182,484 B2 | 2/2007 | Buelow | |
| 7,190,863 B2 | 3/2007 | Frankiewicz | |
| 7,194,184 B2 | 3/2007 | Buelow | |
| 7,198,398 B2 | 4/2007 | Buelow | |
| 7,220,035 B2 | 5/2007 | Buelow | |
| 7,326,188 B1 | 2/2008 | Russell | |
| 7,374,318 B2 | 5/2008 | Brooks | |
| 7,384,165 B2 | 6/2008 | Doyle | |
| 7,524,082 B2 | 4/2009 | North | |
| 7,677,780 B2 | 3/2010 | Lundin | |
| 7,690,331 B2 | 4/2010 | Hurwitz | |
| 7,758,220 B1 | 7/2010 | Grothe | |
| D621,502 S | 8/2010 | Downs | |
| 7,837,069 B2 | 11/2010 | Kroub | |
| 7,901,353 B2 | 3/2011 | Vayser | |
| 8,373,860 B2 * | 2/2013 | Kiesel et al. | 356/417 |
| 2001/0016105 A1 | 8/2001 | Sugiyama | |
| 2002/0054494 A1 | 5/2002 | Ishiharada | |
| 2003/0004469 A1 | 1/2003 | Kraushaar | |
| 2003/0152344 A1 | 8/2003 | Brunet | |

(56) References Cited

U.S. PATENT DOCUMENTS

| | | |
|---|---|---|
| 2003/0222786 A1 | 12/2003 | Dannenmann |
| 2004/0042735 A1 | 3/2004 | Ma |
| 2004/0160774 A1 | 8/2004 | Lionetti |
| 2004/0217586 A1 | 11/2004 | Mastropaolo |
| 2004/0246700 A1 | 12/2004 | Palmer |
| 2005/0011282 A1 | 1/2005 | Voege |
| 2005/0099624 A1* | 5/2005 | Staehr .................... A61M 5/14 356/319 |
| 2005/0171492 A1 | 8/2005 | Rodriquez |
| 2005/0182356 A1 | 8/2005 | Dixon |
| 2005/0230575 A1 | 10/2005 | Zelenski |
| 2006/0013547 A1 | 1/2006 | Kitano |
| 2006/0070458 A1 | 4/2006 | Jones |
| 2006/0147161 A1 | 7/2006 | Kim |
| 2006/0232385 A1 | 10/2006 | Scherer |
| 2007/0103926 A1 | 5/2007 | Brooks |
| 2007/0106263 A1 | 5/2007 | Ward |
| 2008/0097179 A1 | 4/2008 | Russo |
| 2008/0099313 A1 | 5/2008 | Dhir |
| 2008/0115957 A1 | 5/2008 | Duffy |
| 2008/0123323 A1 | 5/2008 | Brunet |
| 2008/0198032 A1 | 8/2008 | North |
| 2009/0177407 A1* | 7/2009 | Lennernas ...................... 702/19 |
| 2009/0284962 A1 | 11/2009 | Grothe |
| 2009/0310123 A1* | 12/2009 | Thomson ............... G01N 33/49 356/40 |
| 2010/0019755 A1 | 1/2010 | Law |
| 2010/0231619 A1 | 9/2010 | Espinoza-Ibarra |
| 2011/0264045 A1 | 10/2011 | Thompson |
| 2013/0208497 A1 | 8/2013 | Provost |

FOREIGN PATENT DOCUMENTS

| | | |
|---|---|---|
| WO | WO 9106255 | 5/1991 |
| WO | WO 99/21600 A2 | 5/1999 |
| WO | WO 01/07435 | 8/2001 |
| WO | WO 2005/051462 | 6/2005 |
| WO | WO 2005/058410 | 6/2005 |
| WO | WO 2005/106899 | 11/2005 |
| WO | WO 2006/060688 A2 | 6/2006 |
| WO | WO 2006/065271 | 6/2006 |

OTHER PUBLICATIONS

*Projects: Mitigating Risks Associated with Multiple IV Infusions*, Centre for Global eHealth Innovation © 2013, 1 page.
AAMI, *Multiple Line Management*, as available at http://www.aami.org/htsi/infusion/wg/multiple.line.html on May 15, 2013, 1 page.
International Report on Patentability, Application No. PCT/US2012/054154, report issued on May 20, 2014, 9 pages.
Katz, Leslie, *Bright Idea: Charging cables light up as a current flows*. www.CNET.com, © CBS Interactive, Feb. 2, 2012, 3 pages.
Dexim, *Visible Green Cable for iPad/iPhone/iPod*, © 2011, dexim, Inc., 2 pages, as available at http://dexim.net/usproducts/V-Green/DWA065.html.
Notification of Transmittal of the International Search Report and the Written Opinion of the International Searching Authority or the Declaration, Application No. PCT/US2012/065154, mailed Apr. 12, 2013, 3 pages.
European Search Report, Application No. 12848985.3, 7 pages, dated Sep. 9, 2015.
Chinese Office Action, Application No. 201280067143.3, dated Sep. 1, 2015, 7 pages.
Supplementary European Search Report, EP Application No.: 12848985, completed Dec. 21, 2015, 15 pages.

* cited by examiner

SYSTEMS AND METHODS FOR ILLUMINATED MEDICAL TUBING DETECTION AND MANAGEMENT INDICATING A CHARACTERISTIC OF AT LEAST ONE INFUSION PUMP

RELATED APPLICATION

This application is a continuation-in-part of U.S. application Ser. No. 13/296,883 filed Nov. 15, 2011, which is hereby fully incorporated herein by reference.

TECHNICAL FIELD

This disclosure relates generally to medical devices. More particularly, this disclosure relates to systems for, and methods of, medical tubing detection and management.

BACKGROUND

In critical care environments, a single patient can be connected to multiple infusion pumps or other tubing-based delivery or removal systems at the same time. Because of this, a multitude of medical tubing can be near and around the patient, making it difficult for medical professionals to know which tubing relates to which infusion pump, delivery system, or removal system. Further, parameters such as route of infusion, drug interaction, and whether the line is putting fluid into the patient's body or carrying fluid away from the patient's body, for example, are critical to the care of a patient. If the wrong medication is placed in the wrong set of tubing, the results can be fatal. Thus, the organization and identification of tubing lines is vitally important.

Currently, the identification of tubing lines is done by hand, often by a medical professional hand-tracing the tubing from a delivery or removal device, through the span of tubing, and to the patient, or vice-versa. With respect to infusion systems, the medical industry has devised standardized colors and patterns to indicate characteristics of medical tubing, like route of infusion and type of tube. Thus, more updated methods of identifying tubing involve hand-labeling a tubing line with these standardized markings by adhering a label to the line after initial implementation or the tracing described above. In some instances, a single line of tubing can have multiple labels affixed to it. However, the human-executed practices described above are not only time-consuming, but also prone to mistakes in labeling or identification due to human error and a lack of robustness in or reliability of adhesive labels and other rudimentary visual identification schemes.

Additionally, even when the multitude of lines are labeled correctly, there remains a difficulty in reading and evaluating the labels when the room in which the patient resides is not well lighted. For example, when a medical professional enters a patient's darkened room, such as when the patient is sleeping at night, in order to check the connectivity or status of one or more of the lines, the professional will often have to turn the overhead room lights on, or have a supplementary light to position on the lines and labels, like a flashlight. The turning on of room lights or use of a flashlight around the patient may be disruptive to the patient's sleep. Additionally, the use of a flashlight can be cumbersome, especially when both of the professional's hands are needed for patient care. Further, some drugs are sensitive to the wavelength of certain light, thereby limiting the types of lights that may be used around medical lines.

In addition, existing medical tubing provides no indication of the operating status or, in cases of problems with the tubing or infusion, alerts for the attending medical professional. In order to check the operating status of the infusion device and attached tubing, the medical professional must first inspect the device, inspect the interface to the tubing, and subsequently trace along the tubing to evaluate a proper flow. Similarly, medical professionals are often not alerted when there is a problem with the tubing or infusion; the entire length of tubing must be visually inspected for blockages or occlusions. Thus, in addition to the problem of identifying existing medical tubing, a problem exists in identifying operating and problem statuses.

Further, medical tubing detection and management has heretofore been problematic for medical practitioners. In hospitals, for example, there may be a large number of tubes, cords, and cables present in patient care areas—particularly in those areas or rooms where patients are receiving intensive care. A relatively easy and efficient way of identifying and organizing medical and infusion tubing is therefore desirable, along with identification of corresponding tubing sets and drug infusion routes. Such information could be vitally important in, e.g., determining acceptable compatibilities and desired interactions of drugs being administered to a patient.

Therefore, there is a need for an automated, safe, and effective way of identifying medical tubing, as well as for identifying any operating statuses or problem statuses with the flow of the medical liquid within the tubing. There is also therefore a need for systems for, and methods of, medical tubing detection and management.

SUMMARY

Embodiments relate to illuminated medical tubing, such that individual medical lines are identifiable based on an illumination or color scheme. This disclosure also describes novel and inventive systems for, and methods of, medical tubing detection and management.

In an embodiment, a medical tubing set comprises a fluid conduit adapted to convey a medical fluid, an optical element coupled to the fluid conduit and configured to provide illumination, and a power source configured to power the optical element.

In an embodiment, a method of operating a medical tubing set comprises installing the medical tubing set in a medical device at a first end and in a patient at a second end, setting at least one operating parameter of the medical tubing set, sensing at least one characteristic of the medical tubing set, comparing the at least one sensed characteristic against the at least one operating parameter, and illuminating the medical tubing set based on at least the comparison of the at least one sensed characteristic and the at least one operating parameter.

In an embodiment of a method of operating a medical tubing set, the medical tubing set comprising a fluid conduit adapted to convey a medical fluid, an optical element coupled to the fluid conduit and configured to provide illumination, and a power source configured to power the optical element, the method comprises installing the medical tubing set in a medical device at a first end and in a patient at a second end; providing a source of power with the power source; applying the source of power to the optical element; and illuminating the fluid conduit with the optical element.

The subject matter hereof thereby improves the way medical tubing is identified in a critical care environment. Because the tubing provides a visual indication, no hand-tracing of tubing from, e.g., the infusion device, through the span of tubing, and into the patient is required. Additionally, labels adhered to the tubing, or other rudimentary visual identification schemes, are no longer needed to identify characteristics of the tube, like route of infusion and type of tube; these characteristics can be indicated by the illumination component. Likewise, because the tubing is illuminated, the tubing is identifiable even in a darkened room, and thus no supplementary light is needed to identify individual tubes or labels. Further, sensors integrated into the tubing, like pressure sensors, occlusion sensors, fluid flow sensors, temperature sensors, liquid density sensors, air bubble sensors, salinity sensors, pH sensors, dissolved oxygen sensors, conductivity sensors, and electrolyte sensors, for example, provide data about the tubing and fluid that can be accumulated and subsequently reported as a visual indication by the illumination component. In this way, emergency situations can be instantaneously expressed by a visual indication. Manufacturing advantages also exist in embodiments. Existing medical tubing manufacturing can be modestly altered or supplemented in order to produce the tubing of the subject matter hereof. Similarly, in embodiments, existing medical devices and medical tubing can be retrofit such that the subject matter hereof is usable on devices and tubing not originally designed for it. In another advantage, various components of embodiments are highly reusable, thus lowering the cost to practitioners.

The most common source of occlusions is a clamp on the medical tubing that is previously applied to the tubing but subsequently forgotten by hospital staff. Consequently, in another advantage, when a clamp is placed on embodiments, the clamp also acts as a stimulus for the passing illumination by blocking, altering, restricting, or otherwise changing the optical path. As a result, in embodiments, the passing illumination is mostly terminated, and thereby highlighted, at the forgotten clamp. Embodiments can thus provide a readily discernable visual indication of forgotten clamps.

In an embodiment, a system for medical tubing detection and management could include an infusion manifold housing having at least one fluid channel therethrough. At least one fluid input port could be provided in the infusion manifold housing, and the at least one fluid input port could be configured to connect fluidically to illuminated medical tubing and be in fluidic communication with the at least one fluid channel through the infusion manifold housing. A fluid output port could be provided in the infusion manifold housing, and the fluid output port could be configured to be in fluidic communication with the at least one fluid channel through the infusion manifold housing. At least one photosensor could be provided in the infusion manifold housing, and the at least one photosensor could be configured to receive light from the illuminated medical tubing that is connected to the at least one fluid input port; and the fluid output port could be configured to connect fluidically to fluid output tubing.

In another embodiment, a system for medical tubing detection and management could include an infusion manifold housing having at least one fluid channel therethrough. At least one fluid input port could be provided in the infusion manifold housing, and the at least one fluid input port could be configured to connect fluidically to illuminated medical tubing and be in fluidic communication with the at least one fluid channel through the infusion manifold housing. A fluid output port could be provided in the infusion manifold housing, and the fluid output port could be configured to be in fluidic communication with the at least one fluid channel through the infusion manifold housing. At least one photosensor could be provided in the infusion manifold housing, and the at least one photosensor could be configured to receive light from the illuminated medical tubing that is connected to the at least one fluid input port; and the fluid output port could be configured to connect fluidically to fluid output tubing. The at least one photosensor could generate an output signal in response to light received from the illuminated medical tubing.

In another embodiment, a system for medical tubing detection and management could include an infusion manifold housing having at least one fluid channel therethrough. At least one fluid input port could be provided in the infusion manifold housing, and the at least one fluid input port could be configured to connect fluidically to illuminated medical tubing and be in fluidic communication with the at least one fluid channel through the infusion manifold housing. A fluid output port could be provided in the infusion manifold housing, and the fluid output port could be configured to be in fluidic communication with the at least one fluid channel through the infusion manifold housing. At least one photosensor could be provided in the infusion manifold housing, and the at least one photosensor could be configured to receive light from the illuminated medical tubing that is connected to the at least one fluid input port; and the fluid output port could be configured to connect fluidically to fluid output tubing. The at least one photosensor could generate an output signal in response to light received from the illuminated medical tubing. At least one infusion pump could be fluidically connected to the illuminated medical tubing. The at least one infusion pump could be configured to generate a light output that is conducted from the illuminated medical tubing to the at least one photosensor in the infusion manifold housing, wherein the light output from the at least one infusion pump is indicative of at least one characteristic of the at least one pump.

In another embodiment, a system for medical tubing detection and management could include an infusion manifold housing having at least one fluid channel therethrough. At least one fluid input port could be provided in the infusion manifold housing, and the at least one fluid input port could be configured to connect fluidically to illuminated medical tubing and be in fluidic communication with the at least one fluid channel through the infusion manifold housing. A fluid output port could be provided in the infusion manifold housing, and the fluid output port could be configured to be in fluidic communication with the at least one fluid channel through the infusion manifold housing. At least one photosensor could be provided in the infusion manifold housing, and the at least one photosensor could be configured to receive light from the illuminated medical tubing that is connected to the at least one fluid input port; and the fluid output port could be configured to connect fluidically to fluid output tubing. The at least one photosensor could generate an output signal in response to light received from the illuminated medical tubing. At least one infusion pump could be fluidically connected to the illuminated medical tubing. The at least one infusion pump could be configured to generate a light output that is conducted from the illuminated medical tubing to the at least one photosensor in the infusion manifold housing, wherein the light output from the at least one infusion pump is indicative of at least one characteristic of the at least one pump. The at least one characteristic of the at least one infusion pump could include an identification of a drug being delivered to a patient.

In another embodiment, a system for medical tubing detection and management could include an infusion manifold housing having at least one fluid channel therethrough. At least one fluid input port could be provided in the infusion manifold housing, and the at least one fluid input port could be configured to connect fluidically to illuminated medical tubing and be in fluidic communication with the at least one fluid channel through the infusion manifold housing. A fluid output port could be provided in the infusion manifold housing, and the fluid output port could be configured to be in fluidic communication with the at least one fluid channel through the infusion manifold housing. At least one light pipe could be provided in the infusion manifold housing. The at least one light pipe could have a first end and a second end, with the first end thereof being optically connected to the at least one fluid input port. At least one lens could be provided in the infusion manifold housing. The at least one lens could be optically connected to the second end of the at least one light pipe and configured to transmit light from the at least one light pipe outwardly from the infusion manifold housing. At least one photosensor could be located externally from the infusion manifold housing. The at least one photosensor could be configured to receive light from the at least one lens; and the fluid output port could be configured to connect fluidically to fluid output tubing.

In another embodiment, a system for medical tubing detection and management could include an infusion manifold housing having at least one fluid channel therethrough. At least one fluid input port could be provided in the infusion manifold housing, and the at least one fluid input port could be configured to connect fluidically to illuminated medical tubing and be in fluidic communication with the at least one fluid channel through the infusion manifold housing. A fluid output port could be provided in the infusion manifold housing, and the fluid output port could be configured to be in fluidic communication with the at least one fluid channel through the infusion manifold housing. At least one light pipe could be provided in the infusion manifold housing. The at least one light pipe could have a first end and a second end, with the first end thereof being optically connected to the at least one fluid input port. At least one lens could be provided in the infusion manifold housing. The at least one lens could be optically connected to the second end of the at least one light pipe and configured to transmit light from the at least one light pipe outwardly from the infusion manifold housing. At least one photosensor could be located externally from the infusion manifold housing. The at least one photosensor could be configured to receive light from the at least one lens; and the fluid output port could be configured to connect fluidically to fluid output tubing. The at least one photosensor could generate an output signal in response to light received from the illuminated medical tubing.

In another embodiment, a system for medical tubing detection and management could include an infusion manifold housing having at least one fluid channel therethrough. At least one fluid input port could be provided in the infusion manifold housing, and the at least one fluid input port could be configured to connect fluidically to illuminated medical tubing and be in fluidic communication with the at least one fluid channel through the infusion manifold housing. A fluid output port could be provided in the infusion manifold housing, and the fluid output port could be configured to be in fluidic communication with the at least one fluid channel through the infusion manifold housing. At least one light pipe could be provided in the infusion manifold housing. The at least one light pipe could have a first end and a second end, with the first end thereof being optically connected to the at least one fluid input port. At least one lens could be provided in the infusion manifold housing. The at least one lens could be optically connected to the second end of the at least one light pipe and configured to transmit light from the at least one light pipe outwardly from the infusion manifold housing. At least one photosensor could be located externally from the infusion manifold housing. The at least one photosensor could be configured to receive light from the at least one lens; and the fluid output port could be configured to connect fluidically to fluid output tubing. The at least one photosensor could generate an output signal in response to light received from the illuminated medical tubing. At least one infusion pump could be fluidically connected to the illuminated medical tubing. The at least one infusion pump could be configured to generate a light output that is conducted from the illuminated medical tubing to the at least one photosensor located externally from the infusion manifold housing. The light output from the at least one infusion pump could be indicative of at least one characteristic of the at least one pump.

In another embodiment, a system for medical tubing detection and management could include an infusion manifold housing having at least one fluid channel therethrough. At least one fluid input port could be provided in the infusion manifold housing, and the at least one fluid input port could be configured to connect fluidically to illuminated medical tubing and be in fluidic communication with the at least one fluid channel through the infusion manifold housing. A fluid output port could be provided in the infusion manifold housing, and the fluid output port could be configured to be in fluidic communication with the at least one fluid channel through the infusion manifold housing. At least one light pipe could be provided in the infusion manifold housing. The at least one light pipe could have a first end and a second end, with the first end thereof being optically connected to the at least one fluid input port. At least one lens could be provided in the infusion manifold housing. The at least one lens could be optically connected to the second end of the at least one light pipe and configured to transmit light from the at least one light pipe outwardly from the infusion manifold housing. At least one photosensor could be located externally from the infusion manifold housing. The at least one photosensor could be configured to receive light from the at least one lens; and the fluid output port could be configured to connect fluidically to fluid output tubing. The at least one photosensor could generate an output signal in response to light received from the illuminated medical tubing. At least one infusion pump could be fluidically connected to the illuminated medical tubing. The at least one infusion pump could be configured to generate a light output that is conducted from the illuminated medical tubing to the at least one photosensor located externally from the infusion manifold housing. The light output from the at least one infusion pump could be indicative of at least one characteristic of the at least one pump. The at least one characteristic of the at least one infusion pump could include an identification of a drug being delivered to a patient.

In another embodiment, a system for medical tubing detection and management could include an infusion manifold housing having at least one fluid channel therethrough. At least one fluid input port could be provided in the infusion manifold housing, and the at least one fluid input port could be configured to connect fluidically to illuminated medical tubing and be in fluidic communication with the at least one fluid channel through the infusion manifold housing. A fluid output port could be provided in the infusion manifold housing, and the fluid output port could be configured to be in fluidic communication with the at least one fluid channel through the infusion manifold housing. At least one photosensor could be provided in the infusion manifold housing, and the at least one photosensor could be configured to receive light from the illuminated medical tubing that is connected to the at least one fluid input port; and the fluid output port could be configured to connect fluidically to fluid output tubing. The at least one photosensor could generate an output signal in response to light received from the illuminated medical tubing. At least one infusion pump could be fluidically connected to the illuminated medical tubing. The at least one infusion pump could be configured to generate a light output that is conducted from the illuminated medical tubing to the at least one photosensor in the infusion manifold housing, wherein the light output from the at least one infusion pump is indicative of at least one characteristic of the at least one pump. The system could be characterized in that the system could be configured to identify each of a plurality of infusion pumps that are connected, by the illuminated medical tubing, respectively, to each of the at least one fluid input port in the infusion manifold housing.

In another embodiment, a system for medical tubing detection and management could include an infusion manifold housing having at least one fluid channel therethrough. At least one fluid input port could be provided in the infusion manifold housing, and the at least one fluid input port could be configured to connect fluidically to illuminated medical tubing and be in fluidic communication with the at least one fluid channel through the infusion manifold housing. A fluid output port could be provided in the infusion manifold housing, and the fluid output port could be configured to be in fluidic communication with the at least one fluid channel through the infusion manifold housing. At least one light pipe could be provided in the infusion manifold housing. The at least one light pipe could have a first end and a second end, with the first end thereof being optically connected to the at least one fluid input port. At least one lens could be provided in the infusion manifold housing. The at least one lens could be optically connected to the second end of the at least one light pipe and configured to transmit light from the at least one light pipe outwardly from the infusion manifold housing. At least one photosensor could be located externally from the infusion manifold housing. The at least one photosensor could be configured to receive light from the at least one lens; and the fluid output port could be configured to connect fluidically to fluid output tubing. The at least one photosensor could generate an output signal in response to light received from the illuminated medical tubing. At least one infusion pump could be fluidically connected to the illuminated medical tubing. The at least one infusion pump could be configured to generate a light output that is conducted from the illuminated medical tubing to the at least one photosensor located externally from the infusion manifold housing. The light output from the at least one infusion pump could be indicative of at least one characteristic of the at least one pump. The system could be characterized in that the system could be configured to identify each of a plurality of infusion pumps that are connected, by the illuminated medical tubing, respectively, to each of the at least one fluid input port in the infusion manifold housing.

In another embodiment, a method of medical tubing detection and management could include providing a system for medical tubing detection and management. The system could include an infusion manifold housing having at least one fluid channel therethrough. At least one fluid input port could be provided in the infusion manifold housing, and the at least one fluid input port could be configured to connect fluidically to illuminated medical tubing, and be in fluidic communication with the at least one fluid channel through the infusion manifold housing. A fluid output port could be provided in the infusion manifold housing, and the fluid output port could be configured to be in fluidic communication with the at least one fluid channel through the infusion manifold housing. At least one photosensor could be provided in the infusion manifold housing. The at least one photosensor could be configured to receive light from the illuminated medical tubing that is connected to the at least one fluid input port and generate an output signal in response thereto. The fluid output port could be configured to connect fluidically to fluid output tubing. The at least one infusion pump could be fluidically connected to the illuminated medical tubing. The at least one infusion pump could be configured to generate a light output that is conducted from the illuminated medical tubing to the at least one photosensor in the infusion manifold housing. The light output from the at least one infusion pump could be indicative of at least one characteristic of the at least one pump. The at least one characteristic of the at least one infusion pump could include an identification of a drug being delivered to a patient from the fluid output tubing.

In another embodiment, a method of medical tubing detection and management could include providing a system for medical tubing detection and management. The system could include an infusion manifold housing having at least one fluid channel therethrough. At least one fluid input port could be provided in the infusion manifold housing, and the at least one fluid input port being could be configured to connect fluidically to illuminated medical tubing, and be in fluidic communication with the at least one fluid channel through the infusion manifold housing. A fluid output port could be provided in the infusion manifold housing, and the fluid output port could be configured to be in fluidic communication with the at least one fluid channel through the infusion manifold housing. At least one light pipe could be provided in the infusion manifold housing; and the at least one light pipe could have a first end and a second end, and the first end thereof could be optically connected to the at least one fluid input port. At least one lens could be provided in the infusion manifold housing, and the at least one lens could be optically connected to the second end of the at least one light pipe and configured to transmit light from the at least one light pipe outwardly from the infusion manifold housing. At least one photosensor could be located externally from the infusion manifold housing. The at least one photosensor could be configured to receive light from the at least one lens and generate an output signal in response thereto. The fluid output port could be configured to connect fluidically to fluid output tubing. The at least one infusion pump could be fluidically connected to the illuminated medical tubing. The at least one infusion pump could be configured to generate a light output that is conducted from the illuminated medical tubing to the at least one photosensor located externally from the infusion manifold housing. The light output from the at least one infusion pump could be indicative of at least one characteristic of the at least one pump. The at least one characteristic of the at least one infusion pump could include an identification of a drug being delivered to a patient from the fluid output tubing.

The above summary of the subject matter hereof is not intended to describe each illustrated embodiment or every implementation thereof. The figures and the detailed description that follow more particularly exemplify these embodiments.

BRIEF DESCRIPTION OF THE DRAWINGS

The subject matter hereof may be more completely understood in consideration of the following detailed description of various embodiments in connection with the accompanying drawings, in which.

Figure 1A:
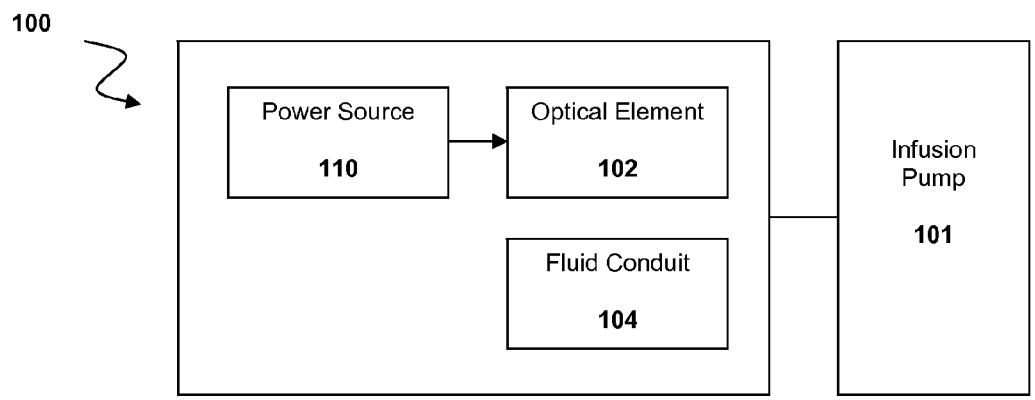
FIG. 1A depicts a block diagram of a tubing set system according to an embodiment.

While the subject matter hereof is amenable to various modifications and alternative forms, specifics thereof have been shown by way of example in the drawings and will be described in detail. It should be understood, however, that the intention is not to limit the subject matter hereof to the particular embodiments described but rather to cover all modifications, equivalents, and alternatives falling within the spirit and scope of the subject matter hereof as defined by the appended claims.

DETAILED DESCRIPTION

Embodiments relate to an illuminated medical tubing set that provides visual indications of characteristics relating to the type and operating status of the tubing. In embodiments, single and dual lumen tubing can be used. In one dual lumen embodiment, one lumen is used is used as the lighted channel, and the other lumen is used to transport the drug or fluid. In another embodiment, an inner lumen is nested within an outer lumen, whereby either the inner lumen is used as the lighted channel and the outer lumen is used as the fluid conduit, or the outer lumen is used as the lighted channel and the inner lumen is used as the fluid conduit. The inside surface of a single channel of tubing is optically coated with a side-emitting material in another embodiment. In such an embodiment, a single channel is utilized as the conduit for both the transportation of the fluid and the transportation of the light or color. In another embodiment, the outside surface of a single channel of tubing is optically coated with a side-emitting material. Both the outside and inside surfaces of a single channel of tubing are optically coated with a side-emitting material in another embodiment. In yet another embodiment, a segment of electroluminescent (EL) wire is coupled to medical tubing such that, when current is passed through the EL wire, the wire and consequently, the adjoining tubing, are illuminated. Light-emitting diodes (LEDs) are positioned at opposite ends of or along the tubing in order to illuminate the length of tubing in another embodiment. Various other combinations and configurations of these and other components can be implemented in other embodiments.

Embodiments also relate to systems for, and methods of, medical tubing detection and management, that may provide relatively easy and efficient ways of identifying and organizing medical and infusion tubing, identifying corresponding tubing sets and drug infusion routes, and determining acceptable compatibilities and desired interactions of drugs being administered to a patient.

Figure 1B:
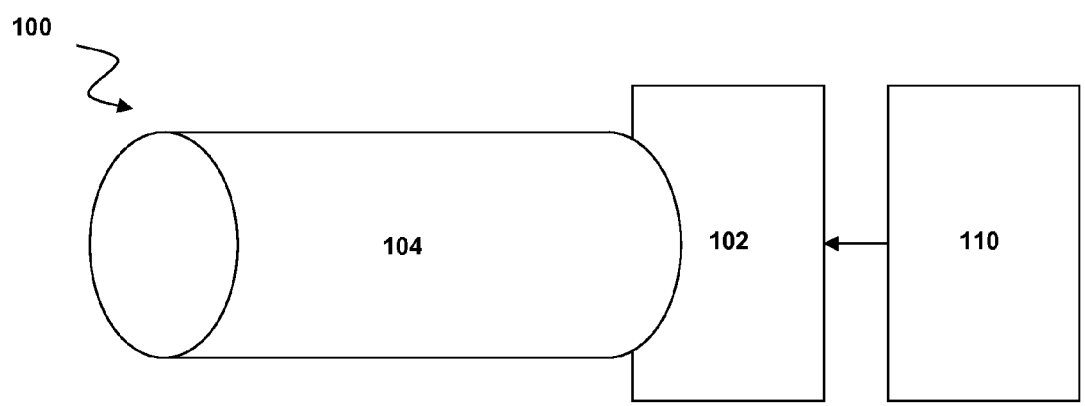
FIG. 1B depicts a block diagram of a tubing set system according to an embodiment.
Figure 1C:
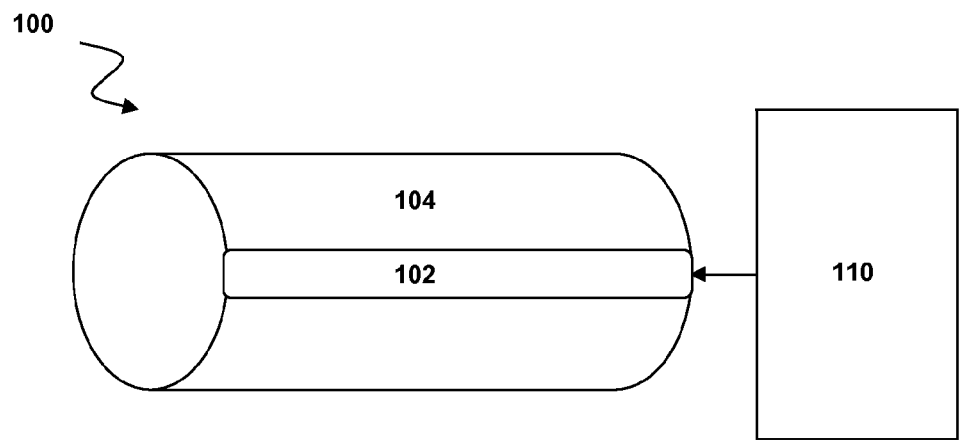
FIG. 1C depicts a block diagram of a tubing set system according to an embodiment.
Figure 2:
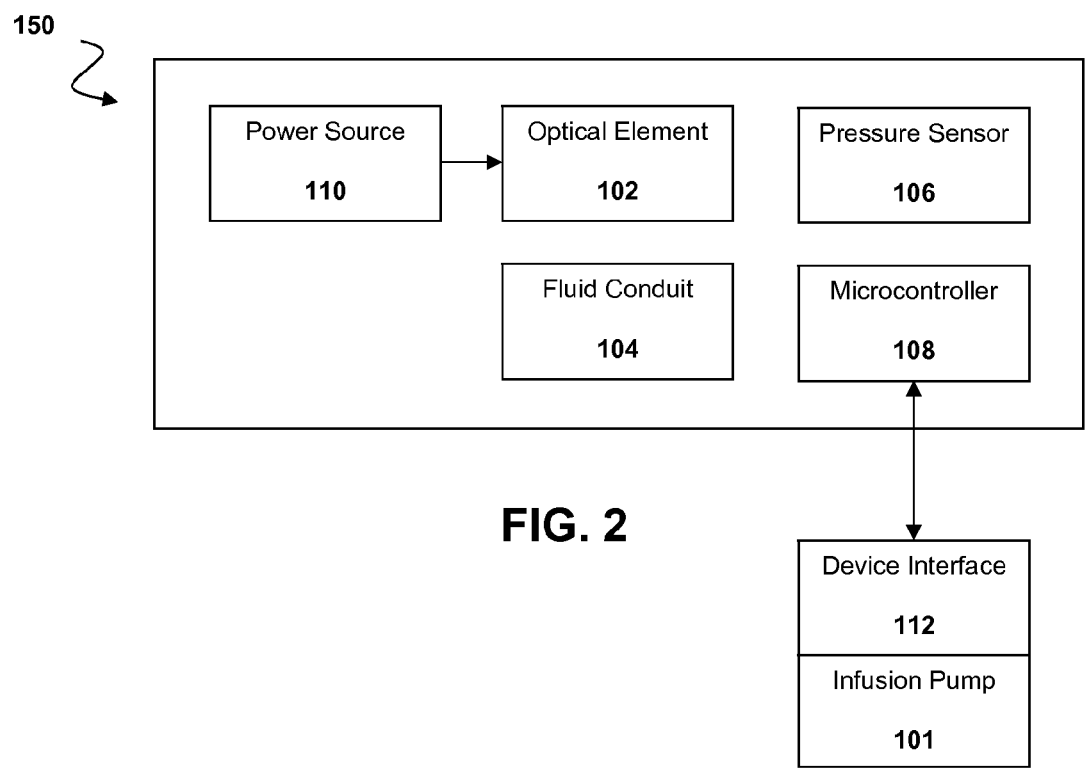
FIG. 2 depicts a block diagram of a tubing set system according to an embodiment.

Referring generally to FIGS. 1A-1C, block diagrams of an illuminated tubing set system 100 are depicted, according to embodiments. Embodiments of illuminated tubing set system 100 generally comprise an optical element 102, a fluid conduit 104, and a power source 110. Example embodiments of illuminated tubing set 100 are described below. In general, power source 110 interfaces with optical element 102, and optical element 102 is configured to illuminate tubing set 100. Optionally, and as depicted in FIG. 2, in another embodiment, illuminated tubing set 150 can further comprise a pressure sensor 106 and a microcontroller 108. Additional sensors, such as to monitor other characteristics of the tubing, fluid, or surrounding environment, can also be included in other embodiments. For example, an occlusion sensor, temperature sensor, flow sensor, liquid density sensor, air bubble sensor, salinity sensor, pH sensor, dissolved oxygen sensor, conductivity sensor, electrolyte sensor, or any combination thereof, can be included in embodiments.

In another embodiment (not depicted), illuminated tubing set 150 can comprise optical element 102, fluid conduit 104, power source 110, and one or more sensors, without microcontroller 108. Further, one or more sensors can comprise, for example, a pressure sensor, occlusion sensor, temperature sensor, flow sensor, liquid density sensor, air bubble sensor, salinity sensor, pH sensor, dissolved oxygen sensor, conductivity sensor, electrolyte sensor, or any combination thereof. In embodiments without microcontroller 108, an integrated circuit (IC) or other generic chip can optionally be included. The IC is configured to provide information to device interface 112 via an electronic signal. In an embodiment, the IC can provide identifying information such as part number, lot number, or expiration date, for example.

Referring again to FIG. 1A, optical element 102 provides an illuminated visual indicator for tubing set 100. In embodiments, optical element 102 runs continuously and lengthwise for the length of tubing set 100, as depicted, for example, in FIG. 1C. The visual indicator in embodiments could therefore be substantially as bright and illuminated at the midpoint of tubing set 100 as it is at the interface to power source 110. For example, in an embodiment, optical element 102 comprises a side-emitting optical coating running the length of tubing set 100 and a light-generating element, such as a laser or other concentrated light source. In such an embodiment, power source 110 powers the light-generating element, which directs light along the side-emitting optical coating. Light is reflected along the length of tubing set 100 to illuminate tubing set 100. The optical coating can comprise an adhesive acrylate-based cladding solution, or any other coating appropriate for a plastic or silicone substrate. In an embodiment, the optical path for optical element 102 is co-extruded with fluid conduit 104 at the time of manufacture. In another embodiment, optical element 102 comprises an illuminated EL wire running the length of tubing set 100. In another embodiment, optical element 102 is positioned at discrete points along tubing set 100, for example, and comprises one or more illuminable LEDs, such as multi-color LEDs. In such an embodiment, power source 110 powers discrete lights or indicator elements at certain illumination points, for example, at the interface point with power source 110, as depicted, for example, in FIG. 1B. Both a greater number and lesser number of illumination points are considered. For example, optical element 102 points can be at the interface with power source 110 and near the patient contact site. In another example, illumination points can be at the interface point with power source 110, at the midpoint of tubing set 100, and near the infusion or patient contact site.

Optical element 102 can be configured to provide white light or colored light, or to provide no light, or to selectively alternate between one or more lighted and/or non-lighted settings. Further, optical element 102 can provide varying degrees of brightness. In certain situations, like when a patient's room is darkened—at night, for example—the brightness of optical element 102 can be reduced. The reduced intensity light of optical element 102 is still easily visible in the darkened ambient lighting, yet not bright enough to disturb the patient. Conversely, when the ambient lighting is brightened—during the day, for example—the brightness of optical element 102 can be increased to increase the ease of visibility of tubing set 100. Additionally, optical element 102 can be configured to provide flashing or patterned light. Examples of such flashing or patterned light are given below. Additional optical elements, like a chemiluminescent fluid, can also be included in other embodiments.

Fluid conduit 104 is used to transmit fluid in a critical care environment. For example, fluid conduit 104 can transmit medication from an infusion pump 101 to a patient. Alternatively, fluid conduit 104 can provide the conveyance for removing fluid from a patient. Fluid conduit 104 generally comprises a cylinder with a diameter wide enough for fluid to flow appropriately for the medical application. Thus, fluid conduit 104 can have diameters of different sizes in various embodiments. For example, fluid conduit 104 having diameters of about 0.015 inches to about 3.0 inches are contemplated. Other diameters are also considered. Fluid conduit 104 is typically made of a flexible silicon plastic appropriate for a medical environment, such that it is odorless, tasteless, and inert. Further, fluid conduit 104 is nonreactive to body tissues and fluids and can withstand repeated sterilizations. Other appropriate materials are also considered, like polyvinyl chloride or any other appropriate thermoplastic polymer. Fluid conduit 104 can also be of varying lengths, depending on the medical application. In embodiments, fluid conduit 104 can provide the conveyance for both the medical fluid as well as the housing for optical element 102. Typically, fluid conduit 104 is clear or transparent so that the fluid flowing throughout fluid conduit 104 is visible through the walls of the cylinder. In other embodiments, however, fluid conduit 104 can be partially or fully translucent or opaque.

Power source 110 provides a source of the power for optical element 102. In embodiments, power source 110 can be integrated into the medical device to which tubing set 100 interfaces. In other embodiments, power source 110 can be integrated within the body of fluid conduit 104 or another portion of tubing set 100 itself. Power source 110 generates or conveys the power required of the particular embodiment of optical element 102. For example, power source 110 can be a battery. In another example, power source 110 is an electrical connection to the power source of the medical device.

In an embodiment, for example one in which optical element 102 comprises a light-generating element and a side-emitting optical coating from which light can reflect, power source 110 is a battery that powers the light-generating element. A beam of focused light is directed by the light-generating element appropriately along the sides of the conduit of the optical coating to illuminate tubing set 100. In another embodiment, power source 110 comprises a source of alternating current, where optical element 102 comprises, for example, a length of EL wire. The alternating current is applied to the EL wire to illuminate the wire, the conduit housing optical element 102 and thus, tubing set 100. In another embodiment, power source 110 includes a voltage source designed to power an LED, where optical element 102 comprises an LED. The above-described power sources are provided for example only and are not intended to be limiting for power source 110. Any appropriate power source can be used. For example, in embodiments, direct current, battery, photovoltaic, linear regulated, switched mode power sources, or any other useful power source can be utilized.

In embodiments, and referring to FIG. 2, tubing set 150 can further comprise pressure sensor 106. Pressure sensor 106 is used to monitor the pressure of the fluid within fluid conduit 104. By measuring the pressure, emergency or alertable situations can be detected for the fluid flow within fluid conduit 104. In embodiments (not depicted), a tubing set can comprise any useful sensor, for example, occlusion sensor, temperature sensor, flow sensor, liquid density sensor, air bubble sensor, salinity sensor, pH sensor, dissolved oxygen sensor, conductivity sensor, electrolyte sensor, or any combination thereof. Similar to the above-described monitoring of pressure sensor 106, any of the aforementioned sensors can monitor fluid conduit 104 and subsequently relay emergency or alertable situations, depending on the specifics of the respective sensor.

In embodiments, tubing set 150 can further comprise microcontroller 108. Microcontroller 108 is used to capture the pressure sensed by pressure sensor 106. Algorithms regarding pressure changes can be programmed into microcontroller 108. In an example, if the measured pressure is outside of a particular boundary or the measured delta is outside limits placed on a previously-measured acceptable value, an alert situation may be present. Further, microcontroller 108 provides an interface to control power source 110. In this way, various colored lights or flashing patterns can be implemented. In the alert situation described above, microcontroller 108 can signal to power source 110 that a non-standard operating status should be indicated. Myriad algorithms can be implemented, given this framework, to alert and provide status of the operation of the tubing set. Examples are given herein below.

Device interface 112 can provide an interface for programming basic operation, alarm indicators (including appropriate limits), colors, and other operating parameters into microcontroller 108. In an embodiment, device interface 112 is implemented as part of a medical device, such as an infusion pump 101. In another embodiment, device interface 112 is implemented as a stand-alone component of tubing set 150.

Device interface 112 can be configured to provide standardized operating parameters to microcontroller 108. Standardized profiles or configurations having standardized operation, alarm indications, colors, and other operating parameters can be implemented for each medical device for a particular hospital site. Each type of medical device can have a specific profile with operating parameters unique to that device. Similarly, a specific profile can be developed for each set of tubing implemented having a specific sensor or set of sensors. Device interface 112 can be configured to install these profiles, and thereby adjust the operating settings, prior to the use of the medical device. For example, a particular hospital could standardize all occlusion pressure alarms to flash tubing set 150 with the color red. Such a configuration allows for uniformity across an entire hospital site, thus further easing burden on medical professionals and further providing value with tubing set 150 use. At that particular hospital site, all medical professionals would know that a flashing red tubing set indicates an occlusion problem.

Figure 3:
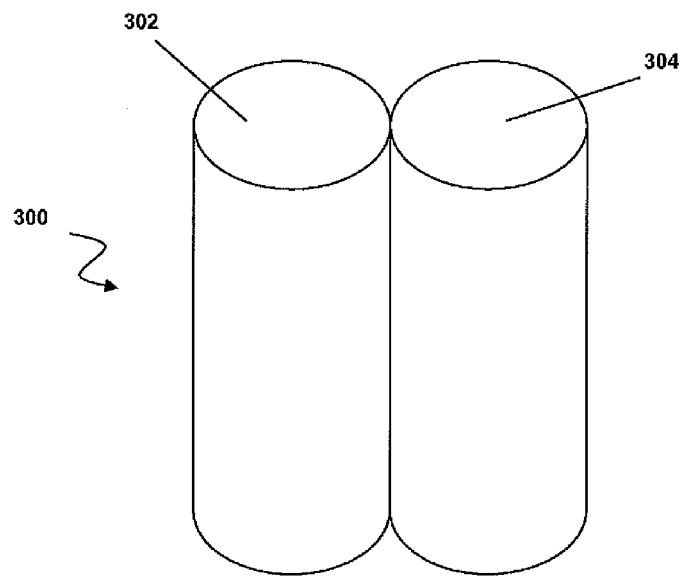
FIG. 3 is a perspective view of a dual lumen tubing set according to an embodiment.

Referring to FIG. 3, an embodiment of a dual lumen tubing set 300 is depicted. Dual lumen tubing set 300 generally comprises an optical interface 302 and a fluid conduit 304. Optical interface 302 can be, for example as described above with respect to optical interface 102, a fiber optic channel, a length of EL wire extending throughout the channel, or a series of LEDs placed along the channel, among others. Optical interface 302 and fluid conduit 304 are immediately adjacent each other in one embodiment so that when optical interface 302 is illuminated, fluid conduit 304 is also illuminated.

Figure 4:
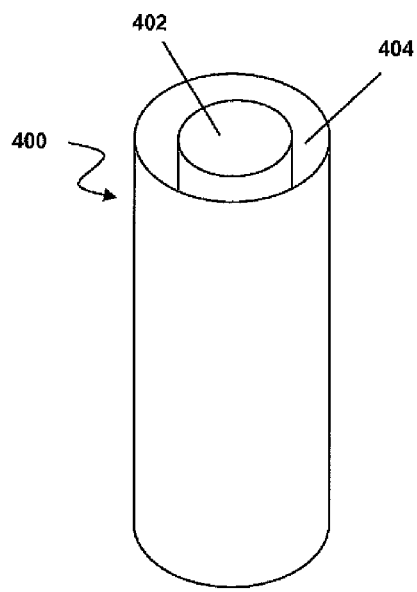
FIG. 4 is a perspective view of a tubing set utilizing an inner lumen and an outer lumen according to an embodiment.

Referring to FIG. 4, an embodiment of a dual lumen tubing set 400 is depicted. Dual lumen tubing set 400 generally comprises an inner lumen 402 and an outer lumen 404. Inner lumen 402 is nested within outer lumen 404 such that inner lumen 402 is completely enclosed by outer lumen 404. In an embodiment, inner lumen 402 provides the fluid conduit and outer lumen 404 provides the housing for the optical interface for dual lumen tubing set 400. When illuminated using appropriately clear or transparent lumens, the optical element in outer lumen 404 illuminates inner lumen 402 and the fluid flowing throughout. In another embodiment, inner lumen 402 provides the housing for the optical interface and outer lumen 404 provides the fluid conduit for dual lumen tubing set 400. When illuminated, the optical element in inner lumen 402 illuminates outer lumen 404 and the fluid flowing throughout. In embodiments, the optical interface can be, as described above with respect to optical interface 102, a fiber optic channel, a length of EL wire extending throughout the channel, or a series of LEDs placed along the channel. In other nested embodiments (not depicted), additional lumens can extend throughout the outermost lumen, with multiple fluids flowing throughout, depending on the medical application. Whichever lumen is chosen as the fluid conduit can illuminate the remaining fluid conduit lumens.

Figure 5:
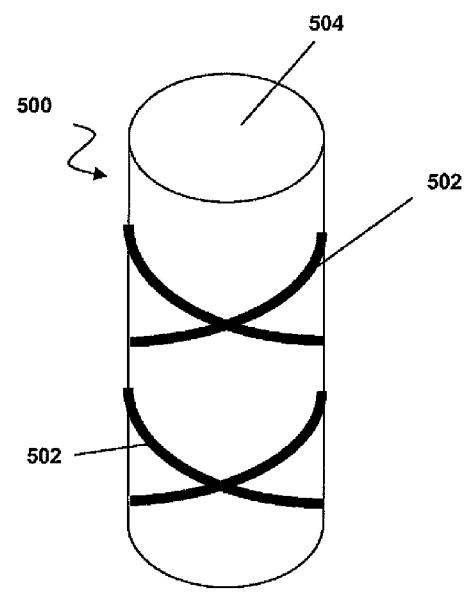
FIG. 5 is a perspective view of a tubing set utilizing an electroluminescent (EL) wire according to an embodiment.
Figure 6:
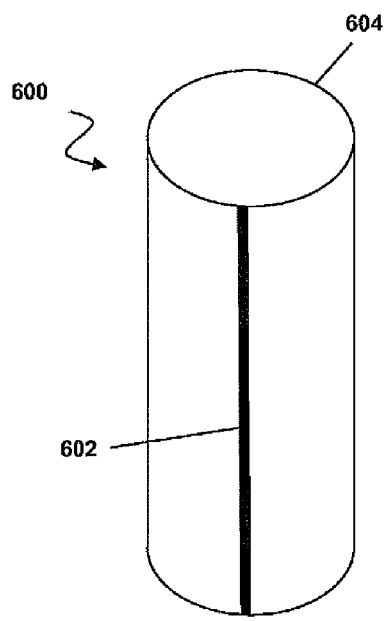
FIG. 6 is a perspective view of a tubing set utilizing an EL wire according to an embodiment.

Referring to FIG. 5, an embodiment of tubing set 500 using an EL wire is depicted. Tubing set 500 generally comprises an optical element 502 and a fluid conduit 504. In such an embodiment, optical element 502 is a length of EL wire. Optical element 502 is encircled around and coupled to the outer wall of fluid conduit 504 in a crisscrossing pattern. Similarly, referring to FIG. 6, another embodiment of a tubing set 600 using EL wire is depicted. Tubing set 600 generally comprises an optical element 602 and a fluid conduit 604. Again, in such an embodiment, optical element 602 is a length of EL wire. Optical element 602 is coupled to the outer wall of fluid conduit 604 along one side of the outer wall. When optical element 502 or optical element 602 are illuminated, respective fluid conduits 504 or 604 are similarly illuminated. In operation, to illuminate optical element 502 or 602 and thus fluid conduit 504 or 604, an alternating current is applied to one end of the EL wire of optical element 502 or 602.

Figure 7:
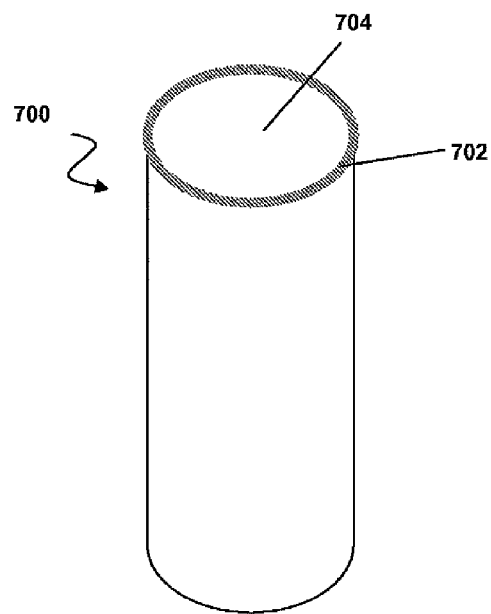
FIG. 7 is a perspective view of a tubing set utilizing an interior optical coating according to an embodiment.

Referring to FIG. 7, an embodiment of tubing set 700 comprising a side-emitting optical coating is depicted. Tubing set 700 generally comprises an optical element 702 and a fluid conduit 704. In such an embodiment, optical element 702 comprises a side-emitting optical coating and a light-generating element. The side-emitting coating of optical element 702 is coated along the inside walls of fluid conduit 704. The combination of the light-generating element and the optical coating, when light is directed by the light-generating element along the coated walls of fluid conduit 704 provides an illuminated fluid conduit 704. Tubing set 700 therefore has a single conduit; fluid conduit 704 provides the conveyance for both the medical fluid as well as the housing for the optical element.

Figure 8A:
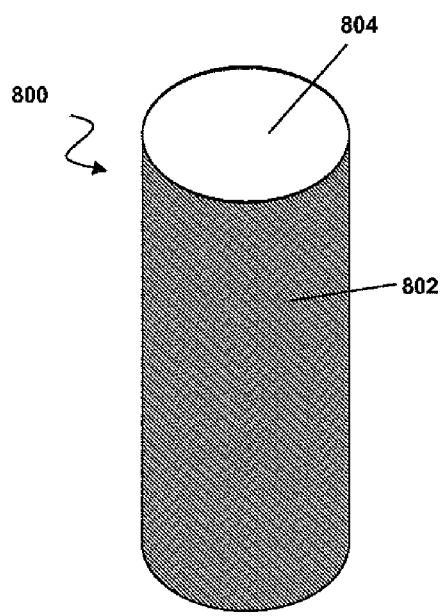
FIG. 8A is a perspective view of a tubing set utilizing an exterior optical coating according to an embodiment.

Similarly, referring to FIG. 8A, an embodiment of tubing set 800 also comprising an optical coating is depicted. Tubing set 800 generally comprises an optical element 802 and a fluid conduit 804. Similar to tubing set 700, optical element 802 comprises a side-emitting optical coating and a light-generating element. However, unlike tubing set 700, tubing set 800 has the optical coating along the outer wall of fluid conduit 804.

In operation, to illuminate fluid conduit 704 or 804, a beam of focused light is directed appropriately at one end of fluid conduit 704 or 804 by the light-generating element of optical element 702 or 802, respectively, so that the light reflects along the coated sides of fluid conduit 704 or 804, respectively.

Figure 8B:
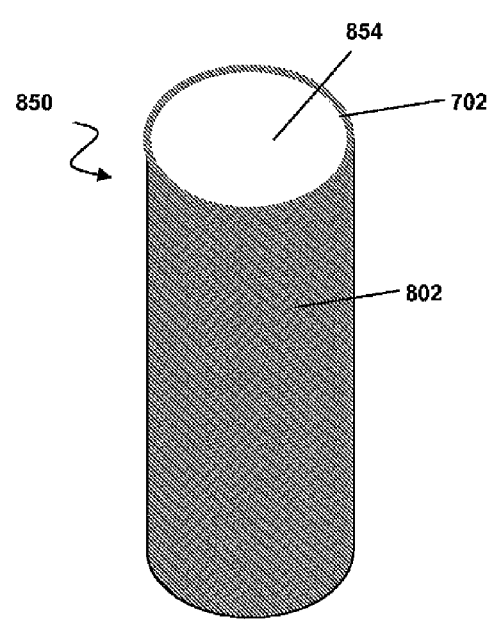
FIG. 8B is a perspective view of a tubing set utilizing both an interior optical coating and an exterior optical coating according to an embodiment.

Referring to FIG. 8B, an embodiment of tubing set 850 also comprising an optical coating is depicted. Tubing set 850 is a combination of tubing set 700 and tubing set 800. Tubing set 850 generally comprises an inside optical element 702 and an outside optical element 802, both optical elements 702 and 802 comprising a coating of side-emitting material such that there is optical coating on both the interior and exterior of the tubing wall, and a fluid conduit 854. In tubing set 850, the tube wall itself comprises the optical path.

In operation, to illuminate fluid conduit 854, a beam of focused light is directed appropriately within the wall of fluid conduit 854 by the light-generating element of optical element 702 or 802, respectively, so that the light reflects within the coated sides of fluid conduit 854. The combination of the light-generating element and the two optical coatings, when light is directed by the light-generating element within the wall of fluid conduit 854 provides an illuminated fluid conduit 854.

Figure 9:
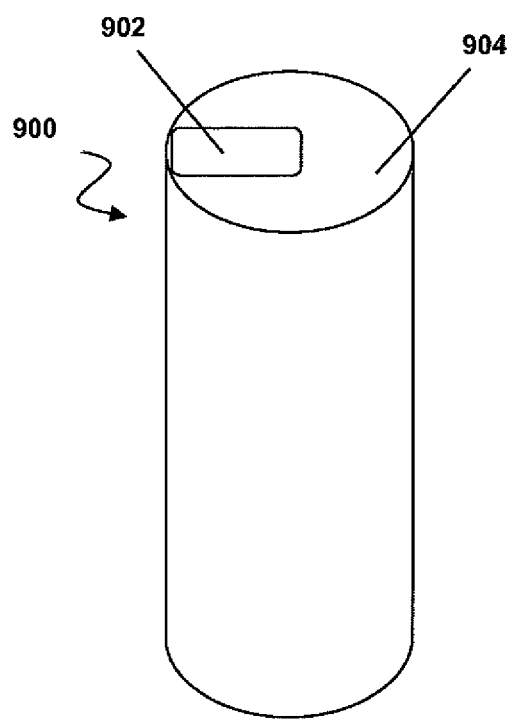
FIG. 9 is a perspective view of a tubing set utilizing light-emitting diodes (LEDs) according to an embodiment.

Referring to FIG. 9, an embodiment of tubing set 900 having one or more LEDs is depicted. Tubing set 900 generally comprises an optical element 902 and a fluid conduit 904. In such an embodiment, optical element 902 comprises at least one LED. As depicted, optical element 902 is positioned near an opening of fluid conduit 904, though other positionings, configurations, and arrangements are possible in other embodiments. As appropriate, additional optical elements 902 can be positioned along fluid conduit 904 to provide consistent illumination of fluid conduit 904 when optical elements 902 are illuminated. In operation, to illuminate optical element 902, a voltage is applied to the LED to thereby illuminate the LED and fluid conduit 904.

Figure 10:
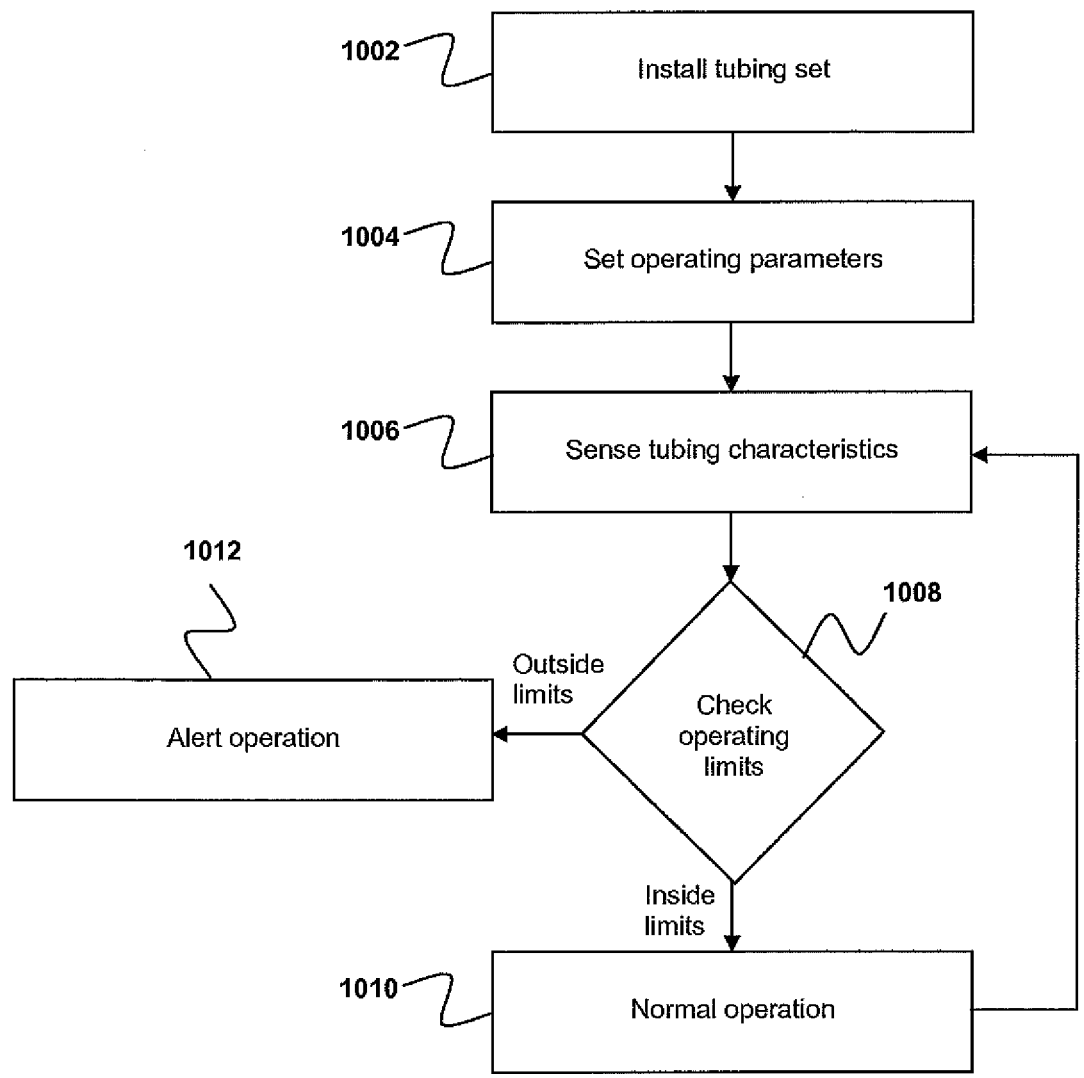
FIG. 10 is a flowchart of the operation of a tubing set according to an embodiment.

In operation generally, referring to FIG. 10, a tubing set is installed at 1002. Depending on the embodiment and application, installation can be any variation of securely coupling one end of the tubing set to a medical device, such as an infusion pump 101, and the opposite end to a patient, or as a drain from a patient to a waste-capturing device. Fluid conduit 104 is appropriately coupled to the fluid source. Further, optical element 102 and power source 110 are appropriately coupled together if required. For example, one installation can be connecting an infusion pump 101 to a patient at an infusion site. Infusion pump 101 can have an integrated power source 110 that is operably couplable to the optical element 102 of the tubing itself. Another installation can be connecting a feeding device to a patient at a feeding site where the tubing itself contains the power source 110, not the feeding device. Upon correct installation, the tubing set can illuminate or flash a known pattern or sequence to indicate correct installation.

At 1004, operating parameters are set. The color of tube, illumination intensity, and alarm limits for the various coupled sensors, and other operating parameters are programmed into microcontroller 108 via device interface 112. In some embodiments, the operating parameters are set automatically upon installation of the tubing set. For example, because of the standardization of colors and patterns in the medical industry, any tubing set connected to a specific device requiring a standard color or pattern can automatically be programmed by the device via device interface 112 to set microcontroller 108 with the standardized illumination, standard limits, and standard intensity for the application, without any additional human intervention. If the medical professional desires a different color scheme limits, or intensity, device interface 112, which can reside on a medical device, or as a separate interface, can be utilized to program microcontroller 108.

At 1006, an initial set of tubing characteristics are sensed. If pressure sensor 106 is present in the tubing set embodiment, as depicted in FIG. 2, the pressure of the tube is sensed. Further, or alternatively, any additional sensors, as described above, are activated to capture their respective sensor indications. At 1008, a check of operating limits is conducted. The decision point at 1008 is utilized to ensure that operation of the tube is within the set limits. This type of limit or boundary check is conducted for all attached sensors, or if desired, fewer than all attached sensors. If, for example, the pressure sensed by pressure sensor 106 is inside of expected limits, normal operation results at 1010. Normal operation 1010 can include a solid illumination at the desired programmed light intensity, or no illumination, if desired. If, however, the pressure sensed by pressure sensor 106 is outside of expected limits, alert operation results at 1012. Alert operation 1012 can include a flashing or patterned illumination to indicate some sort of problem with the tubing set. For example, a quicker flash might indicate a pressure or occlusion problem, whereas a slower flash might indicate a temperature problem. In another example, a pattern of three quick flashes followed by a pause of no illumination might indicate an improperly connected tubing set. In yet another example, a short flash followed by a long flash might indicate a microcontroller 108 fault. Any number of flashing or patterned flashes can be implemented to indicate status. Further, any attached medical device can utilize the illumination capability of the tubing set to indicate status for the medical device by operation via device interface 112.

In either the case of normal operation 1010 or alert operation 1012, power source 110 interfaces with optical element 102 to illuminate optical element 102 and the tubing set. When the tubing set is in normal operation, the recursive loop from normal operation at 1010 back to sense tubing characteristics at 1006 can be conducted in real time, or upon expiration of a standard or programmed wait period. Further, in operation, any of the operating parameters can be adjusted while the tubing set is in use.

Figure 11:
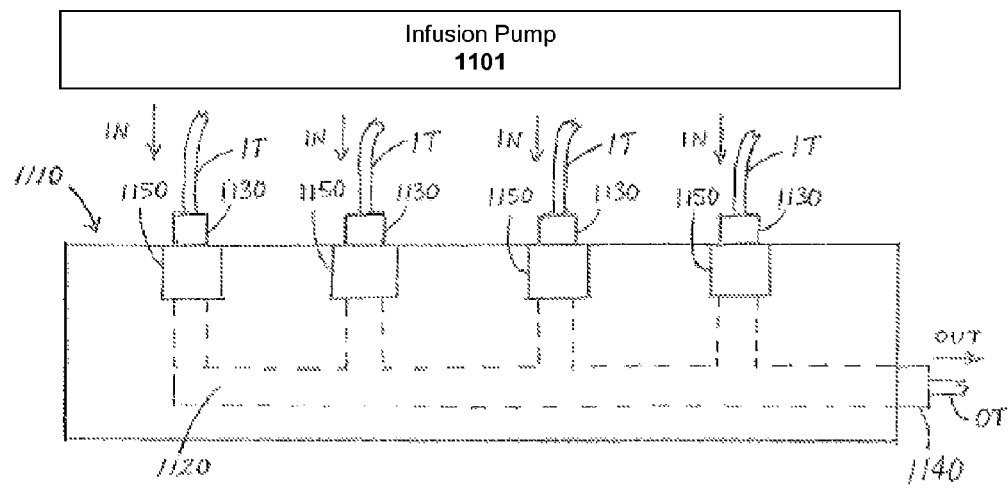
FIG. 11 is an illustration of an embodiment of a system for medical tubing detection and management.

With reference now to FIG. 11, a system for medical tubing detection and management 1100 could include an infusion manifold housing 1110 having at least one fluid channel 1120 therethrough. At least one fluid input port 1130 could be provided in infusion manifold housing 1110. Each input port 1130 could be configured to connect fluidically to illuminated medical tubing IT, respectively, and be in fluidic communication with fluid channel 1120 through infusion manifold housing 1110. As used throughout this document, the term "illuminated medical tubing" includes any suitable illuminated or otherwise optically identifiable medical tubing or lines used with, e.g., infusion pumps, substance delivery systems, and substance removal systems, such as those described by example or otherwise contemplated herein. A fluid output port 1140 could be provided in infusion manifold housing 1110, and be configured to be in fluidic communication with fluid channel 1120 through infusion manifold housing 1110. Fluid output port 1140 could also be configured to connect fluidically to fluid output tubing OT. As used throughout this document, the phrases "connect fluidically" and "fluidic communication" are intended to refer to connections, and conduits or means of transmission, that satisfactorily facilitate movement of fluid through or between intended paths and locations. At least one photosensor 1150 could be provided in infusion manifold housing 1110. As used throughout this document, the term "photosensor" includes any suitable devices that are capable of sensing or detecting light or other electromagnetic energy such as, e.g., optical sensors and photodetectors. Each photosensor 1150 could be configured to receive light from the illuminated medical tubing IT that is connected, respectively, to each fluid input port 1130 (that is, in turn, associated respectively with each photosensor 1150). Each photosensor 1150 could generate an output signal (not depicted in the drawing) in response to light received from the illuminated medical tubing IT. Such output signal could be, for example, transmitted to a computer or other display means by any suitable signal processing or transmission techniques (e.g., wireless transmitters and receivers) for organizing infusion sets or drug compatibility verification as will be described. It is to be appreciated and understood that at least one infusion pump 1101 could be fluidically connected to the illuminated medical tubing IT. In such an application of system 1100, each infusion pump 1101 could be configured to generate a light output (not depicted) that would be conducted from the illuminated medical tubing IT associated with that pump 1101 to each respective photosensor 1150 in housing 1110. The light output from each infusion pump 1101 could be indicative of at least one characteristic of the pump 1101, as will be described below.

Figure 12:
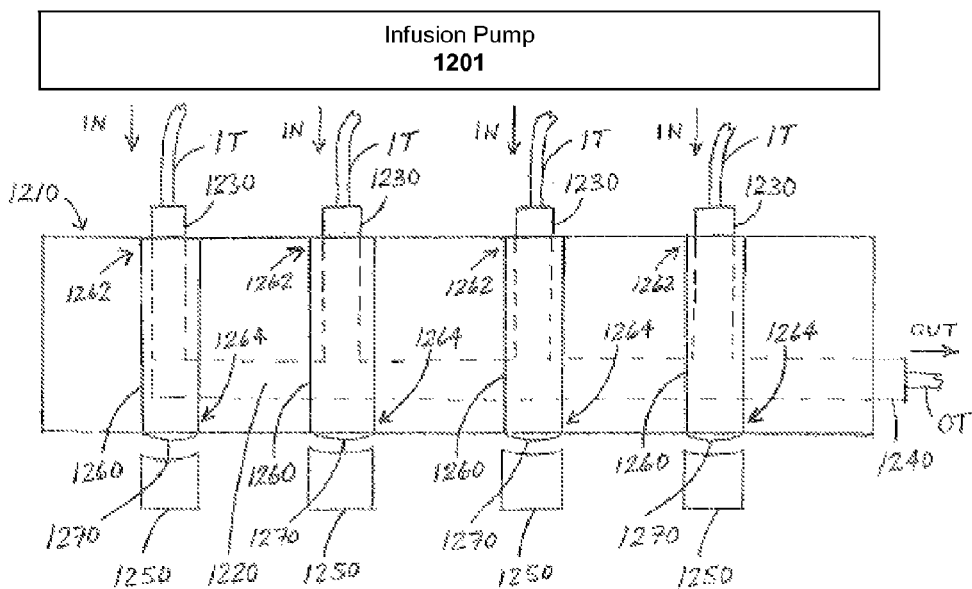
FIG. 12 is an illustration of another embodiment of a system for medical tubing detection and management.

Referring now to FIG. 12, a system for medical tubing detection and management 1200 could include an infusion manifold housing 1210 having at least one fluid channel 1220 therethrough. At least one fluid input port 1230 could be provided in infusion manifold housing 1210. Each input port 1230 could be configured to connect fluidically to illuminated medical tubing IT, respectively, and be in fluidic communication with fluid channel 1220 through infusion manifold housing 1210. A fluid output port 1240 could be provided in infusion manifold housing 1210, and be configured to be in fluidic communication with fluid channel 1220 through infusion manifold housing 1210. Fluid output port 1240 could also be configured to connect fluidically to fluid output tubing OT. At least one light pipe 1260 could be provided in infusion manifold housing 1210. As used throughout this document, the term "light pipe" is intended to include any suitable means or devices for conducting or transmitting light through, or between, intended paths and locations. Each light pipe 1260 could have a first end 1262 and a second end 1264; and the first end 1262 could be optically connected to each fluid input port 1230, respectively. As used throughout this document, the term "optically connected" is intended to refer to connections, and conduits or means of transmission, that satisfactorily facilitate transmission of light through or between intended paths and locations. At least one lens 1270 could be included in infusion manifold housing 1210. Each lens 1270 could be optically connected to second end 1264 of each light pipe 1260, respectively, and be configured to transmit light from each light pipe 1260, respectively, outwardly from infusion manifold housing 1210. At least one photosensor 1250 could be provided externally from infusion manifold housing 1210. In this regard, it is to be appreciated and understood that manifold housing 1210 and its associated, aforedescribed components could be deemed to be disposable—or for a single use or for use with a single patient—while each of the potentially more expensive photosensors 1250 could be reused since they are remote and separate from disposable housing 1210. Thus in one embodiment, although not illustrated, photosensors 1250 could be contained within a sensor housing as part of a pump racking device or be provided on, e.g., an intravenous apparatus or bedside utility pole. Irrespective of a particular embodiment, generally each photosensor 1250 could be configured to receive light from each lens 1270 and the illuminated medical tubing IT that is connected, respectively, to each fluid input port 1230 (that is, in turn, associated respectively with each light pipe 1260). Each photosensor 1250 could generate an output signal (not depicted in the drawing) in response to light received from the illuminated medical tubing IT. Such output signal could be, for example, transmitted to a computer or other display means by any suitable signal processing or transmission techniques (e.g., wireless transmitters and receivers) for organizing infusion sets or drug compatibility verification as will be described. It is to be appreciated and understood that at least one infusion pump 1201 could be fluidically connected to the illuminated medical tubing IT. In such an application of system 1200, each infusion pump 1201 could be configured to generate a light output (not depicted) that would be conducted from the illuminated medical tubing IT associated with that pump 1201 to each respective photosensor 1250 located externally from housing 1210. The light output from each infusion pump 1201 could be indicative of at least one characteristic of the pump 1201, as is next described below.

Referring to both FIGS. 11 and 12, it is to be appreciated and understood that the output signal from each photosensor 1150 or 1250, that could be transmitted to a computer or other display means as aforementioned, could provide a relatively easy and efficient way of organizing infusion sets and providing drug compatibility verification to medical practitioners utilizing system 1100 or 1200. In particular, light output from infusion pumps 1101 or 1201 being received by sensors 1150 or 1250 could be indicative of at least one characteristic of each pump 1101 or 1201 such as, e.g., an identification of a drug being delivered to a patient or a "route of infusion" to the patient. For example, a particular system 1100 or 1200 could be designated as "Epidural Only"; and if a pump 1101 or 1201 for an intravenous drug was erroneously connected to that system 1100 or 1200, then an alarm signal could be generated from each sensor 1150 or 1250 before such incompatible or adverse drug is delivered to the patient.

An example of a method of medical tubing detection and management could include a step of providing a system for medical tubing detection and management such as, e.g., shown in FIG. 11. The system could include an infusion manifold housing having at least one fluid channel therethrough. At least one fluid input port could be in the infusion manifold housing, and be configured to connect fluidically to illuminated medical tubing and be in fluidic communication with each fluid channel in the infusion manifold housing. A fluid output port could be in the infusion manifold housing and be configured to be in fluidic communication with each fluid channel in the infusion manifold housing, and to connect fluidically to fluid output tubing. At least one photosensor could be in the infusion manifold housing. Each photosensor could be configured to receive light from the illuminated medical tubing that is connected to each fluid input port and generate an output signal in response thereto. This example of a method could also include a step of fluidically connecting at least one infusion pump 1101 to the illuminated medical tubing. Each infusion pump 1101 could be configured to generate a light output that is conducted from the illuminated medical tubing to each respective photosensor in the infusion manifold housing. The light output from each infusion pump 1101 could be indicative of at least one characteristic of each pump 1101; and each pump characteristic could include, e.g., an identification of a drug being delivered to a patient from the fluid output tubing.

Another example of a method of medical tubing detection and management could include a step of providing a system for medical tubing detection and management such as, e.g., shown in FIG. 12. The system could include an infusion manifold housing having at least one fluid channel therethrough. At least one fluid input port could be in the infusion manifold housing, and be configured to connect fluidically to illuminated medical tubing and be in fluidic communication with each fluid channel in the infusion manifold housing. A fluid output port could be in the infusion manifold housing and be configured to be in fluidic communication with each fluid channel in the infusion manifold housing, and to connect fluidically to fluid output tubing. At least one light pipe, having a first end and a second end, could be in the infusion manifold housing. A first end of each light pipe could be optically connected to each fluid input port, respectively. At least one lens could also be in the infusion manifold housing. Each lens could be optically connected to the second end of each light pipe, respectively, and be configured to transmit light from each light pipe, respectively, outwardly from the infusion manifold housing. At least one photosensor could be located externally from the infusion manifold housing. Each photosensor could be configured to receive light from each lens, respectively, and generate an output signal in response thereto. This example of a method could also include a step of fluidically connecting at least one infusion pump 1201 to the illuminated medical tubing. Each infusion pump 1201 could be configured to generate a light output that is conducted from the illuminated medical tubing to each respective photosensor located externally from the infusion manifold housing, via the respective light pipes and lenses. The light output from each infusion pump 1201 could be indicative of at least one characteristic of each pump 1201; and each pump characteristic could include, e.g., an identification of a drug being delivered to a patient from the fluid output tubing.

Irrespective of a particular embodiment, it is to be appreciated and understood that systems for, and methods of, medical tubing detection and management—as described by example or otherwise contemplated herein—may be generally characterized in that the systems and methods could be configured to identify each of a plurality of infusion pumps that are connected, by illuminated medical tubing, respectively, to each fluid input port in the infusion manifold housing. It is also to be appreciated and understood that the systems and methods may thus further facilitate the organization and communication of visual indications of characteristics relating to the types and operating statuses of the illuminated medical tubing as described herein or as disclosed in the aforecited co-pending application Ser. No. 13/296,883.

Although not particularly illustrated in FIG. 11 or 12, it is to be appreciated and understood that aforedescribed embodiments of illuminated medical tubing (such as, e.g., various embodiments of single and dual lumen tubing as described herein) may be used individually or in various combinations with systems for, and methods of, medical tubing detection and management, as described or otherwise contemplated herein.

Further, although not illustrated, it is to be appreciated and understood that systems for, and methods of, medical tubing detection and management, as described or otherwise contemplated herein, could include any of the usual attributes of an infusion set manifold such as, e.g., fittings, seals, luer locks, and stopcocks, etc. Also, it is to be appreciated and understood that systems for, and methods of, medical tubing detection and management, as described or otherwise contemplated herein, could also include any desired sensors to monitor characteristics of the tubing, fluid, or surrounding environment (e.g., the aforementioned pressure sensors, occlusion sensors, fluid flow sensors, temperature sensors, liquid density sensors, air bubble sensors, salinity sensors, pH sensors, dissolved oxygen sensors, conductivity sensors, and electrolyte sensors) whether individually or in any desired combinations.

Although illustrated in FIGS. 11 and 12 as embodiments with four tubing inputs, it is to be appreciated and understood that systems for, and methods of, medical tubing detection and management, as described or otherwise contemplated herein, could include any desired number of tubing inputs provided that such systems and methods satisfactorily function as aforedescribed. Analogously, any number of systems for medical tubing detection and management could be employed in a particular care setting, as may be desired for, e.g., maintaining readily identifiable organization of a relatively large number of infusion lines that each could be distinctly and extremely important in treatment of a critically ill patient.

Additionally, it is to be appreciated and understood that tubing outputs of systems for, and methods of, medical tubing detection and management, as described or otherwise contemplated herein, could also be visually identifiable by, e.g., any of the aforedescribed illumination or color scheme techniques of illuminated medical tubing, as may be desired in a particular care setting.

Various embodiments of systems, devices and methods have been described herein. These embodiments are given only by way of example and are not intended to limit the scope of the subject matter hereof. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the subject matter hereof.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the subject matter hereof may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the subject matter hereof, it is expressly intended that the provisions of Section 112, sixth paragraph of 35 U.S.C. are not to be invoked unless the specific terms "means for" or "step for" are recited in a claim.

The invention claimed is:

1. A system for medical tubing detection and management, comprising:
    an infusion manifold housing having at least one fluid channel therethrough;
    at least one fluid input port in said infusion manifold housing, said at least one fluid input port being configured to (i) connect fluidically to medical tubing illuminated external to the infusion manifold housing, and (ii) be in fluidic communication with said at least one fluid channel through said infusion manifold housing;
    a fluid output port in said infusion manifold housing, said fluid output port being configured to be in fluidic communication with said at least one fluid channel through said infusion manifold housing;
    at least one photosensor in said infusion manifold housing, wherein (i) said at least one photosensor is configured to receive light from the illuminated medical tubing that is connected to said at least one fluid input port and generate an output signal in response to the light received from the illuminated medical tubing, and (ii) said fluid output port is configured to connect fluidically to fluid output tubing; and
    at least one infusion pump that is fluidically connected to the illuminated medical tubing, the at least one infusion pump being configured to generate a light output that is conducted from the illuminated medical tubing to said at least one photosensor in said infusion manifold housing, wherein the light output from the at least one infusion pump is indicative of at least one characteristic of the at least one pump.

2. The system for medical tubing detection and management of claim 1, wherein the at least one characteristic of the at least one infusion pump includes an identification of a drug being delivered to a patient.

3. The system for medical tubing detection and management of claim 1, characterized in that said system is configured to identify each of a plurality of infusion pumps that are connected, by said illuminated medical tubing, respectively, to each of said at least one fluid input port in said infusion manifold housing.

4. A system for medical tubing detection and management, comprising:
    an infusion manifold housing having at least one fluid channel therethrough;
    at least one fluid input port in said infusion manifold housing, said at least one fluid input port being configured to (i) connect fluidically to medical tubing illuminated external to the infusion manifold housing, and (ii) be in fluidic communication with said at least one fluid channel through said infusion manifold housing;
    a fluid output port in said infusion manifold housing, said fluid output port being configured to be in fluidic communication with said at least one fluid channel through said infusion manifold housing;
    at least one light pipe in said infusion manifold housing, said at least one light pipe having a first end and a second end, with said first end thereof being optically connected to said at least one fluid input port;
    at least one lens in said infusion manifold housing, said at least one lens being (i) optically connected to said second end of said at least one light pipe and (ii) configured to transmit light from said at least one light pipe outwardly from said infusion manifold housing;

at least one photosensor located externally from said infusion manifold housing, wherein (i) said at least one photosensor is configured to receive light from said at least one lens and generate an output signal in response to the light received from the illuminated medical tubing, and (ii) said fluid output port is configured to connect fluidically to fluid output tubing; and at least one infusion pump that is fluidically connected to the illuminated medical tubing, the at least one infusion pump being configured to generate a light output that is conducted from the illuminated medical tubing to said at least one photosensor located externally from said infusion manifold housing, wherein the light output from the at least one infusion pump is indicative of at least one characteristic of the at least one pump.

5. The system for medical tubing detection and management of claim 4, wherein the at least one characteristic of the at least one infusion pump includes an identification of a drug being delivered to a patient.

6. The system for medical tubing detection and management of claim 4, characterized in that said system is configured to identify each of a plurality of infusion pumps that are connected, by said illuminated medical tubing, respectively, to each of said at least one fluid input port in said infusion manifold housing.

7. A method of medical tubing detection and management, comprising:

providing a system for medical tubing detection and management, including (i) an infusion manifold housing having at least one fluid channel therethrough, (ii) at least one fluid input port in said infusion manifold housing, said at least one fluid input port being configured to (a) connect fluidically to medical tubing illuminated external to the infusion manifold housing, and (b) be in fluidic communication with said at least one fluid channel through said infusion manifold housing, (iii) a fluid output port in said infusion manifold housing, said fluid output port being configured to be in fluidic communication with said at least one fluid channel through said infusion manifold housing, and (iv) at least one photosensor in said infusion manifold housing, wherein (I) said at least one photosensor is configured to receive light from the illuminated medical tubing that is connected to said at least one fluid input port and generate an output signal in response thereto, and (II) said fluid output port is configured to connect fluidically to fluid output tubing; and fluidically connecting at least one infusion pump to the illuminated medical tubing, the at least one infusion pump being configured to generate a light output that is conducted from the illuminated medical tubing to said at least one photosensor in said infusion manifold housing, wherein (i) the light output from the at least one infusion pump is indicative of at least one characteristic of the at least one pump and (ii) the at least one characteristic of the at least one infusion pump includes an identification of a drug being delivered to a patient from said fluid output tubing.

8. A method of medical tubing detection and management, comprising:

providing a system for medical tubing detection and management, including (i) an infusion manifold housing having at least one fluid channel therethrough, (ii) at least one fluid input port in said infusion manifold housing, said at least one fluid input port being configured to (a) connect fluidically to medical tubing illuminated external to the infusion manifold housing, and (b) be in fluidic communication with said at least one fluid channel through said infusion manifold housing, (iii) a fluid output port in said infusion manifold housing, said fluid output port being configured to be in fluidic communication with said at least one fluid channel through said infusion manifold housing, (iv) at least one light pipe in said infusion manifold housing, said at least one light pipe having a first end and a second end, with said first end thereof being optically connected to said at least one fluid input port, (v) at least one lens in said infusion manifold housing, said at least one lens being (a) optically connected to said second end of said at least one light pipe and (b) configured to transmit light from said at least one light pipe outwardly from said infusion manifold housing, and (vi) at least one photosensor located externally from said infusion manifold housing, wherein (I) said at least one photosensor is configured to receive light from said at least one lens and generate an output signal in response thereto, and (II) said fluid output port is configured to connect fluidically to fluid output tubing; and fluidically connecting at least one infusion pump to the illuminated medical tubing, the at least one infusion pump being configured to generate a light output that is conducted from the illuminated medical tubing to said at least one photosensor located externally from said infusion manifold housing, wherein (i) the light output from the at least one infusion pump is indicative of at least one characteristic of the at least one pump and (ii) the at least one characteristic of the at least one infusion pump includes an identification of a drug being delivered to a patient from said fluid output tubing.

* * * * *